United States Patent
Mahar (10) Patent No.: US 9,931,042 B2
(45) Date of Patent: Apr. 3, 2018

(54) MONITORING BABY PHYSICAL CHARACTERISTICS

(71) Applicant: Vivint, Inc., Provo, UT (US)

(72) Inventor: Matthew Mahar, Salt Lake City, UT (US)

(73) Assignee: Vivint Inc., Provo, UT (US)

(*) Notice: Subject to any disclaimer, the term of this patent is extended or adjusted under 35 U.S.C. 154(b) by 0 days.

(21) Appl. No.: 14/961,574

(22) Filed: Dec. 7, 2015

(65) Prior Publication Data
US 2017/0156608 A1    Jun. 8, 2017

(51) Int. Cl.
| | |
|---|---|
| A61B 5/024 | (2006.01) |
| A61B 5/00 | (2006.01) |
| A61B 5/117 | (2016.01) |
| A61B 5/1171 | (2016.01) |
| A61B 5/0205 | (2006.01) |
| A61B 5/11 | (2006.01) |
| A61B 5/113 | (2006.01) |
| G06T 7/00 | (2017.01) |

(52) U.S. Cl.
CPC ........ A61B 5/02416 (2013.01); A61B 5/0022 (2013.01); A61B 5/0205 (2013.01); A61B 5/1128 (2013.01); A61B 5/1135 (2013.01); A61B 5/1176 (2013.01); A61B 5/746 (2013.01); G06T 7/0012 (2013.01); A61B 5/742 (2013.01); A61B 5/7405 (2013.01); A61B 5/7455 (2013.01); A61B 2503/04 (2013.01); A61B 2503/06 (2013.01)

(58) Field of Classification Search
None
See application file for complete search history.

(56) References Cited

U.S. PATENT DOCUMENTS

| | | | | |
|---|---|---|---|---|
| 5,088,497 | A | * 2/1992 | Ikeda | A61B 5/02411 600/453 |
| 5,464,012 | A | * 11/1995 | Falcone | A61B 5/02455 600/301 |
| 7,313,439 | B2 | * 12/2007 | Jackson | A61B 5/02405 600/519 |
| 7,397,380 | B1 | 7/2008 | Smolsky | |
| 8,617,043 | B2 | 12/2013 | Ten Eyck et al. | |
| 9,020,185 | B2 | * 4/2015 | Mestha | A61B 5/0075 382/103 |
| 9,355,214 | B2 | * 5/2016 | Wilson | G06F 19/34 |
| 2013/0001422 | A1 | 1/2013 | Lavon et al. | |
| 2014/0142729 | A1 | 5/2014 | Lobb et al. | |
| 2014/0240511 | A1 | * 8/2014 | Nystrom | H04N 5/33 348/164 |

FOREIGN PATENT DOCUMENTS

WO    2015091582 A1    6/2015

* cited by examiner

*Primary Examiner* — Brian T Gedeon
(74) *Attorney, Agent, or Firm* — Holland & Hart LLP (57) ABSTRACT

The present disclosure relates to systems and methods for monitoring baby physical characteristics. In some embodiments, the method may include projecting light from a video monitoring system toward a monitored user, and detecting a heart rate of the monitored user at the video monitoring system based at least in part on detecting the projected light. The method may further include comparing the detected heart rate with a predetermined heart rate threshold, and initiating an alert based at least in part on the comparing.

18 Claims, 7 Drawing Sheets

MONITORING BABY PHYSICAL CHARACTERISTICS

BACKGROUND

The present disclosure, for example, relates to home security and/or automation systems, and more particularly to providing systems and methods for monitoring baby physical characteristics using monitoring and projected light.

Home automation systems are widely deployed to provide various types of communication and functional features such as monitoring, communication, notification, and/or others. These systems may be capable of supporting communication with a user through a communication connection or a system management action.

Existing video monitoring methods may allow for visual monitoring of a child in the home, but may only provide limited information, such as whether the child is outwardly physically safe or alert. Other, less visible conditions may not be readily observable using current monitoring methods. Other physiological monitoring such as body-worn sensors may also be limited to proper use and positioning. There is a need for a physiological monitoring system to allow for constant and effective physiological monitoring of one or more occupants in the home.

SUMMARY

Known child video monitoring systems may have limited capabilities to monitor physiological parameters of the child, while known body-worn monitoring systems may limit comfort and range of motion for the child. The art lacks a system that combines the freedom of a video monitor with the detailed physiological monitoring capabilities of a body-worn monitor. The present disclosure addresses this and other shortcomings by providing a method for security and/or automation systems, which may include projecting light from a video monitoring system toward a monitored user. The method may further include detecting a heart rate of the monitored user at the video monitoring system based at least in part on detecting the projected light, and comparing the detected heart rate with a predetermined heart rate threshold. The method may further include initiating an alert based at least in part on the comparing. By monitoring one or more users in a home using video monitoring components of the home automation system, the need for individual, wearable sensor units may be avoided, as may the inconvenience and unreliability associated therewith. Instead, the video monitors may "follow" users throughout the home, providing consistent monitoring of various physiological parameters.

In one example, one or more components (e.g., a video monitor, a sensor) may project a light toward the monitored user, and may use the projected light to detect and measure the user's pulse under his skin. This detected pulse rate may be observed over time to detect changes therein, and to associate those changes with one or more predetermined alert condition thresholds. For example, the home automation system may receive the detected pulse rate information over a span of three minutes, and may detect that the monitored user's heart rate has increased by more than 30% during that time. Predetermined alert condition threshold parameters, obtained by one or more connections and/or inputted at the home automation system, may indicate that a change of that magnitude constitutes an urgent alert. The predetermined alert condition threshold parameters may relate to a particular data threshold, such as a minimum pulse rate, or to a particular time threshold, such as a period of time at which an elevated pulse rate is maintained. Other threshold parameters are also envisioned. In some examples, a series of predetermined alert condition threshold parameters may correspond to an alert threshold, for example from a non-urgent alert to an emergency alert, with any number of alert thresholds in-between and/or along the spectrum. Detected alert conditions may be categorized as various alert severities based on predetermined alert severity thresholds. In some examples, these thresholds may be inputted by a user, while in other examples, these thresholds may be determined based on known health standards for an individual of the size, age, etc. of the monitored user, for example pulled from an Internet source. Based on the determination that the detected change in pulse rate magnitude constitutes an urgent alert, the home automation system may issue the alert, for example in the form of an audible and/or visual alarm projected throughout the home and/or to one or more devices, to notify the home occupants of a possible urgent medical condition. Occupants in the home may accordingly tend to the user and seek treatment as necessary.

Additional and/or alternative physiological parameters may be monitored via the video monitoring systems, or one or more sensor units, or a combination thereof, in order to detect a user's current health status, including respiration rate, body temperature, movement data, or auditory data, or a combination thereof. In some examples, the monitored audio data may be used to support or contradict the derived alert condition. For example, a user may be observed experiencing an increased heart rate, but additional detection (of a same and/or a different type, such as audio detection) may indicate that the user is playing with someone else, as indicated, for example, by laughter or other noises and/or video input. On this basis, the system may deduce that an alert condition does not exist, despite the detected heart rate having surpassed a predetermined alert condition threshold. Conversely, an observed user's respiration rate may be stable, but the system may detect that the user is calling for help, and may derive an appropriate alert condition accordingly (indicating the need for some help but not urgent help).

In some examples, facial recognition data may be used in conjunction with the detected physiological parameters in order to identify the user experiencing the alert condition. In particular, the method may include detecting facial data associated with the monitored user, and identifying an identity of the monitored user based at least in part on the detected facial data. This derived user identity information may be communicated along with the alert to one or more users associated with the home automation system. In some examples, the alert may be issued to one or more users outside the home, for example on a mobile computing device and/or at a dispatch call center for emergency providers.

In any example, the issued alert may include at least one of an auditory alert, or a visual alert, or a haptic alert, or a combination thereof. In some examples, detecting the projected light may include analyzing image data captured by the video monitoring system. For example, a captured video image of the monitored user may be analyzed to detect changes in coloration of individual pixels associated with the monitored user's skin. These changes in pixel coloration may be indicative of blood pulsing through the monitored user's arteries, and may be utilized to derive a pulse rate for the monitored user. In some examples, projecting the light toward the monitored user may include projecting the light continuously for a period or projecting the light at predetermined intervals for a period.

In some examples, detecting the heart rate of the monitored user may include detecting the heart rate continuously and/or detecting the heart rate at predetermined intervals. In some examples, the method may include comparing the detected heart rate at a first time with the detected heart rate at a second time, where the alert is initiated based at least in part on the comparing of the detected heart rate at the first time and the second time.

In some examples, the method may include detecting a physiological parameter associated with the monitored user, and comparing the detected physiological parameter with a predetermined physiological parameter threshold. In some examples, detecting the physiological parameter may include detecting at least one of a respiration rate, or a body temperature, or movement data, or auditory data, or a combination thereof. In some examples, the method may further include bypassing the alert based at least in part on comparing the detected physiological parameter with the predetermined physiological parameter threshold. In other examples, the method may further include initiating the alert based at least in part on comparing the detected physiological parameter with the predetermine physiological parameter threshold.

In some examples, the method may further include categorizing the alert based at least in part on comparing the detected physiological parameter with the predetermined physiological parameter threshold. In some examples, the categorizing may include defining the alert as any of a non-urgent alert, or an urgent alert, or an emergency alert, or a combination thereof.

The present disclosure also relates to an apparatus for security and/or automation systems. In some examples, the apparatus may include a processor, memory in electronic communication with the processor, and instructions stored in the memory. In one example, the instructions may be executable by the processor to project light from a video monitoring system toward a monitored user, and detect a heart rate of the monitored user at the video monitoring system based at least in part on detecting the projected light. The instructions may be further executable by the processor to compare the detected heart rate with a predetermined heart rate threshold, and initiate an alert based at least in part on the comparing.

The present disclosure is further related to a non-transitory computer-readable medium storing computer-executable code, the code executable by a processor to project light from a video monitoring system toward a monitored user. The code may be further executable by the processor to detect a heart rate of the monitored user at the video monitoring system based at least in part on detecting the projected light, and to compare the detected heart rate with a predetermined heart rate threshold. The code may be further executable by the processor to initiate an alert based at least in part on the comparing.

The foregoing has outlined rather broadly the features and technical advantages of examples according to this disclosure so that the following detailed description may be better understood. Additional features and advantages will be described below. The conception and specific examples disclosed may be readily utilized as a basis for modifying or designing other structures for carrying out the same purposes of the present disclosure. Such equivalent constructions do not depart from the scope of the appended claims. Characteristics of the concepts disclosed herein—including their organization and method of operation—together with associated advantages will be better understood from the following description when considered in connection with the accompanying figures. Each of the figures is provided for the purpose of illustration and description only, and not as a definition of the limits of the claims.

BRIEF DESCRIPTION OF THE DRAWINGS

A further understanding of the nature and advantages of the present disclosure may be realized by reference to the following drawings. In the appended figures, similar components or features may have the same reference label. Further, various components of the same type may be distinguished by following a first reference label with a dash and a second label that may distinguish among the similar components. However, features discussed for various components—including those having a dash and a second reference label—apply to other similar components. If only the first reference label is used in the specification, the description is applicable to any one of the similar components having the same first reference label irrespective of the second reference label.

DETAILED DESCRIPTION

A system that video monitoring of physiological parameters of a home occupant, utilizing components of a home automation system, is provided below. While existing systems may allow for limited monitoring, either in terms of collectable data or freedom of movement, or both, there is lacking a method by which components of a home automation system may be used to remotely monitor the physiological condition of an occupant. This remote monitoring system may allow for more comprehensive physiological data of the monitored occupant, without the need for body-worn sensors, and utilizing components of the home automation system include video monitoring, audio monitoring, sensors.

The following description provides examples and is not limiting of the scope, applicability, and/or examples set forth in the claims. Changes may be made in the function and/or arrangement of elements discussed without departing from the scope of the disclosure. Various examples may omit, substitute, and/or add various procedures and/or components as appropriate. For instance, the methods described may be performed in an order different from that described, and/or various steps may be added, omitted, and/or combined. Also, features described with respect to some examples may be combined in other examples.

Figure 1:
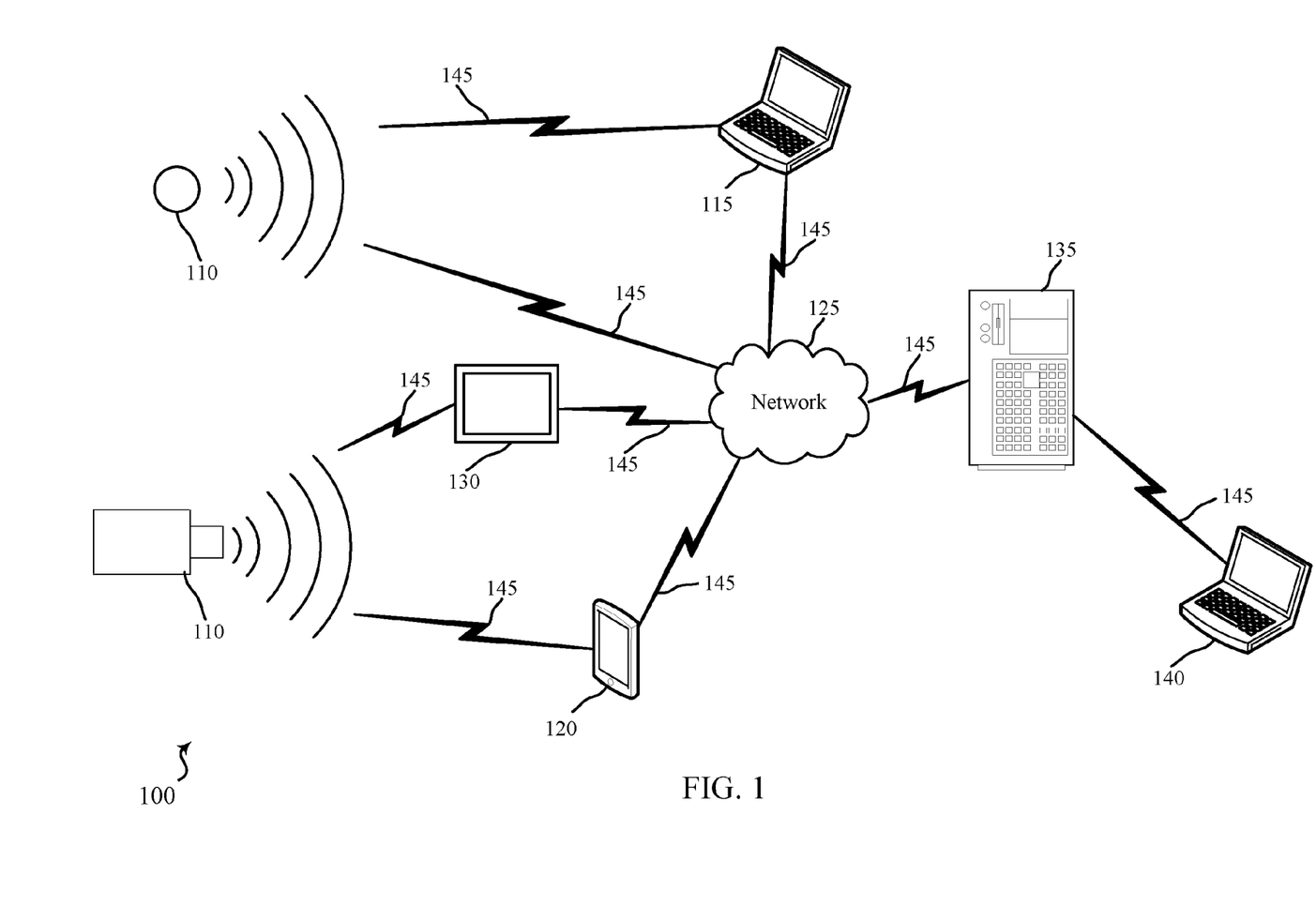
FIG. 1 shows a block diagram relating to an example of a home security and/or automation system, in accordance with various aspects of this disclosure.

FIG. 1 is an example of a security and/or automation system 100 in accordance with various aspects of this disclosure. In some embodiments, the security and/or automation system 100 may include one or more sensor units 110, local computing device 115, 120, network 125, server 135, control panel 130, and remote computing device 140. One or more sensor units 110 may communicate via wired or wireless communication links 145 with one or more of the local computing device 115, 120 or network 125. The network 125 may communicate via wired or wireless communication links 145 with the control panel 130 and the remote computing device 140 via server 135. In alternate embodiments, the network 125 may be integrated with any one of the local computing device 115, 120, server 135, or remote computing device 140, such that separate components are not required.

Local computing device 115, 120 and remote computing device 140 may be custom computing entities configured to interact with one or more sensor units 110 via network 125, and in some embodiments, via server 135. In other embodiments, local computing device 115, 120 and remote computing device 140 may be general purpose computing entities such as a personal computing device, for example, a desktop computer, a laptop computer, a netbook, a tablet personal computer (PC), a control panel, an indicator panel, a multi-site dashboard, an iPod®, an iPad®, a smartphone, a mobile phone, a personal digital assistant (PDA) a smartwatch, a wearable electronic device, and/or any other suitable device operable to send and receive signals, store and retrieve data, and/or execute modules.

Control panel 130 may be a smart home system panel, for example, an interactive panel mounted on a wall in a user's home. Control panel 130 may be in direct communication via wired or wireless communication links 145 with the one or more sensor units 110, or may receive sensor data from the one or more sensor units 110 via local computing devices 115, 120 and network 125, or may receive data via remote computing device 140, server 135, and network 125.

The local computing devices 115, 120 may include memory, a processor, an output, a data input and a communication module. The processor may be a general purpose processor, a Field Programmable Gate Array (FPGA), an Application Specific Integrated Circuit (ASIC), a Digital Signal Processor (DSP), and/or the like. The processor may be configured to retrieve data from and/or write data to the memory. The memory may be, for example, a random access memory (RAM), a memory buffer, a hard drive, a database, an erasable programmable read only memory (EPROM), an electrically erasable programmable read only memory (EEPROM), a read only memory (ROM), a flash memory, a hard disk, a floppy disk, cloud storage, and/or so forth. In some embodiments, the local computing devices 115, 120 may include one or more hardware-based modules (e.g., DSP, FPGA, ASIC) and/or software-based modules (e.g., a module of computer code stored at the memory and executed at the processor, a set of processor-readable instructions that may be stored at the memory and executed at the processor) associated with executing an application, such as, for example, receiving and displaying data from one or more sensor units 110.

The processor of the local computing devices 115, 120 may be operable to control operation of the output of the local computing devices 115, 120. The output may be a television, a liquid crystal display (LCD) monitor, a cathode ray tube (CRT) monitor, speaker, tactile output device, and/or the like. In some embodiments, the output may be an integral component of the local computing devices 115, 120. Similarly stated, the output may be directly coupled to the processor. For example, the output may be the integral display of a tablet and/or smartphone. In some embodiments, an output module may include, for example, a High Definition Multimedia Interface™ (HDMI) connector, a Video Graphics Array (VGA) connector, a Universal Serial Bus™ (USB) connector, a tip, ring, sleeve (TRS) connector, and/or any other suitable connector operable to couple the local computing devices 115, 120 to the output.

The remote computing device 140 may be a computing entity operable to enable a remote user to monitor the output of the sensor units 110. The remote computing device 140 may be functionally and/or structurally similar to the local computing devices 115, 120 and may be operable to receive data streams from and/or send signals to at least one of the one or more sensor units 110 via the network 125. The network 125 may be the Internet, an intranet, a personal area network, a local area network (LAN), a wide area network (WAN), a virtual network, a telecommunications network implemented as a wired network and/or wireless network, etc. The remote computing device 140 may receive and/or send signals over the network 125 via wireless communication links 145 and server 135.

In some embodiments, the one or more sensor units 110 may be sensors configured to conduct periodic or ongoing automatic functions (e.g., identifications, determinations, measurements, etc.) associated with a monitored home occupant, for example a baby or a child. Each sensor unit 110 may be capable of sensing one or more physiological, audio, video, environmental, and/or motion parameters (among other things) associated with the baby, or alternatively, separate sensor units 110 may monitor separate parameters associated with the baby. For example, one sensor unit 110 may measure audio, for example by detecting the sound of the baby crying, coughing, cooing, laughing, and/or the like, while another sensor unit 110 (or, in some embodiments, a different element of the same sensor unit 110) may detect the baby's heart rate and/or respiratory rate, for example by projecting light from the sensor unit 110 toward the baby and/or receiving projected light at the sensor unit 110, and detecting the projected light, for example at a video component of the sensor unit 110 in order to monitor chest expansions and contractions, among other things. In some embodiments, one or more sensor units 110 may additionally monitor alternative parameters associated with the baby and/or the baby's environment, such as room temperature, ambient light levels, and the like. Sensor units 110 may also monitor movement and/or posture data associated with the baby, for example to determine if the baby is sleeping restlessly (based, for example, upon a detected increase in movement such as moving his arms or legs), and/or has stood up in his crib. In still other embodiments, sensor units 110 may be configured to detect facial data associated with the monitored baby and/or other users in order to identify the baby and/or other users. Although described with respect to baby monitoring, these periodic or ongoing automatic measurements could also be performed on an ill or elderly family member, a child, or any other occupant in need of monitoring.

One or more sensor units 110 may detect a monitored user's pulse using detection elements and/or components. For example, the one or more sensor units 110 may utilize, in some examples, Eulerian Video Magnification (EVM), in order to track the variation of individual pixels over time, as recorded, captured, and/or received by the video monitoring component(s) and/or some other components of the one or more sensors units 110. As the monitored user's heart pumps blood throughout his body, his arteries swell with bright red blood, which changes the color of his skin slightly. These per-pixel fluctuations involving a color gradient (e.g., between white and slightly-redder-white) may be detected by the one or more sensor units 110. In some examples, one or more components may convert these pixel fluctuations into a detected heart rate.

In some examples, the amount of reflected light may also be captured and/or received in light data from video and/or other recording methods, may be analyzed, and a change in one or more physiological characteristics may be determined based at least in part on the data and/or the analysis. In some examples, the physiological monitoring may be based at least in part on measurements and/or calculations specific to an individual different times and/or in different contexts. For example, a method may establish a baseline reading at a first time and/or over a first period (which may include one or more measurements during the first period). The method may further establish a second reading at a second time by receiving one or more types of data and may relate this data to a specific user by identifying the user from the baseline reading and/or the second reading. Then, one or more components may compare data from one or more earlier readings with data from the second reading to determine any change in one or more physiological characteristics. In some cases, this comparison may involve comparing earlier-captured video and/or other data with later-captured video and/or other data that has been analyzed to determine differences and/or changes that may be relative to a predetermined threshold and/or other value and/or condition. In some cases, this comparison may involve comparing earlier-captured video and/or other data with later-captured video and/or other data that has been analyzed to determine a trend and/or a correlation based at least in part on the captured data over time. For example, if the baby's heart rate is measured and/or determined to increase by a certain amount (e.g., 10 BPM, 2 BPM/minute) within a predetermined period (e.g., 1 minute, 5 minutes, 10 minutes, 1 hour, etc.) an event condition may be triggered. Other methods for detecting pulse rate using light projection and detection by a camera are also envisioned.

Data gathered by the one or more sensor units 110 may be communicated to local computing device 115, 120, which may be, in some embodiments, a thermostat or other wall-mounted input/output smart home display. In other embodiments, local computing device 115, 120 may be a personal computer or a smartphone, among other things. Where local computing device 115, 120 is a smartphone, the smartphone may have a dedicated application and/or application function directed to receiving and displaying or broadcasting alerts associated with the monitored baby. The local computing device 115, 120 may process the data received from the one or more sensor units 110 to derive an event condition and/or an alert condition. In some embodiments, remote computing device 140 may process the data received from the one or more sensor units 110, via network 125 and server 135, to derive an event condition and/or an alert condition. In some embodiments, live video and/or audio data streams may be communicated from the one or more sensor units 110 to local computing device 115, 120, such that a user may monitor the baby's real-time status without the need for a derived alarm condition. Data transmission may occur via, for example, frequencies appropriate for a personal area network (such as BLUETOOTH® or IR communications) or local or wide area network frequencies such as radio frequencies specified by the IEEE 802.15.4 standard, among others.

In some embodiments, local computing device 115, 120 may communicate with remote computing device 140 or control panel 130 via network 125 and server 135. Examples of networks 125 include cloud networks, local area networks (LAN), wide area networks (WAN), virtual private networks (VPN), wireless networks (using 802.11, for example), and/or cellular networks (using 3G and/or LTE, for example), etc. In some configurations, the network 125 may include the Internet. In some embodiments, a user may access the functions of local computing device 115, 120 from remote computing device 140. For example, in some embodiments, remote computing device 140 may include a mobile application that interfaces with one or more functions of local computing device 115, 120.

The server 135 may be configured to communicate with the one or more sensor units 110, the local computing devices 115, 120, the remote computing device 140, and control panel 130. The server 135 may perform additional processing on signals received from the one or more sensor units 110 or local computing devices 115, 120, or may simply forward the received information to the remote computing device 140 and control panel 130.

Server 135 may be a computing device operable to receive data streams (e.g., from one or more sensor units 110 and/or local computing device 115, 120 or remote computing device 140), store and/or process data, and/or transmit data and/or data summaries (e.g., to remote computing device 140). For example, server 135 may receive a stream of audio data (among other data types) from a sensor unit 110, a stream of physiological data from the same or a different sensor unit 110, and a stream of video data (among other data types) from either the same or yet another sensor unit 110. Physiological data may include heart rate, respiration rate, temperature, posture, and the like. In some embodiments, server 135 may "pull" the data streams, e.g., by querying the sensor units 110, the local computing devices 115, 120, and/or the control panel 130. In some embodiments, the data streams may be "pushed" from the sensor units 110 and/or the local computing devices 115, 120 to the server 135. For example, the sensor units 110 and/or the local computing device 115, 120 may be configured to transmit data as it is generated by or entered into that device. In some instances, the sensor units 110 and/or the local computing devices 115, 120 may periodically transmit data (e.g., as a block of data or as one or more data points).

The server 135 may include a database (e.g., in memory) containing audio, video, physiological, occupancy, profile, medical, past monitoring action(s), and/or other data received from the sensor units 110 and/or the local computing devices 115, 120, among other components. Additionally, as described in further detail herein, software (e.g., stored in memory) may be executed on a processor of the server 135. Such software (executed on the processor) may be operable to cause the server 135 to monitor, process, summarize, present, and/or send a signal associated with the monitored baby data.

Figure 2:
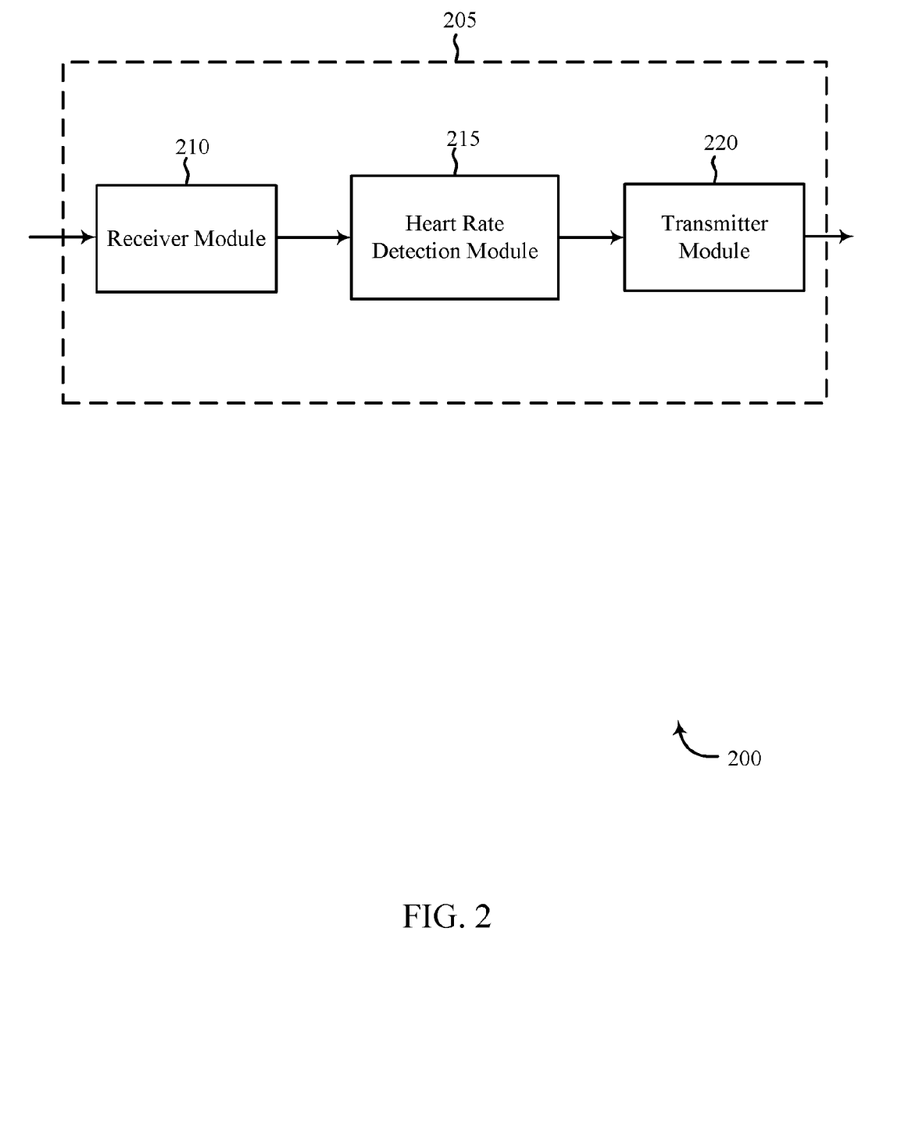
FIG. 2 shows a block diagram of a device relating to a home security and/or automation system, in accordance with various aspects of this disclosure.

FIG. 2 shows a block diagram 200 of an apparatus 205 for use in security and/or automation systems, in accordance with various aspects of this disclosure. The apparatus 205 may be an example of one or more aspects of any of a control panel 130, one or more sensor units 110, local computing device 115, 120, and/or remote computing device 140 described with reference to FIG. 1, among others. The apparatus 205 may include a receiver module 210, a heart rate detection module 215, and/or a transmitter module 220. The apparatus 205 may also be or include a processor. Each of these modules may be in communication with each other, directly and/or indirectly.

The components of the apparatus 205 may, individually or collectively, be implemented using one or more application-specific integrated circuits (ASICs) adapted to perform some or all of the applicable functions in hardware. Alternatively, the functions may be performed by one or more other processing units (or cores), on one or more integrated circuits. In other examples, other types of integrated circuits may be used (e.g., Structured/Platform ASICs, Field Programmable Gate Arrays (FPGAs), and other Semi-Custom ICs), which may be programmed in any manner known in the art. The functions of each module may also be implemented—in whole or in part—with instructions embodied in memory formatted to be executed by one or more general and/or application-specific processors.

The receiver module 210 may receive information such as packets, user data, and/or control information associated with various information channels (e.g., control channels, data channels, etc.). In some embodiments, where the receiver module 210 is an example of one or more aspects of the one or more sensor units 110 of FIG. 1, the receiver module 210 may be configured to detect any of audio, video, light, physiological (including heart rate, respiration rate, posture, sleep status, identity, etc.), and/or movement (including occupancy and location) data (among other things) associated with the baby and/or other monitored user. In other embodiments, where the receiver module 210 is an example of one or more aspects of the local computing device 115, 120, control panel 130, or remote computing device 140, the receiver module 210 may be configured to receive any of audio, video, light, physiological (including heart rate, respiration rate, posture, sleep status, identity, etc.), and/or movement (including occupancy and location) data (among other things) associated with the monitored baby and/or other user, where such data is detected by one or more sensor units positioned near the baby and/or other user. In any embodiment, data associated with the monitored baby and/or user may be passed on to the heart rate detection module 215, and to other components of the apparatus 205.

In some embodiments, heart rate detection module 215 may pass the data associated with the monitored baby received from receiver module 210 directly to transmitter module 220, without processing, for communication to the parent or other monitoring user. For example, where receiver module 210 detects the monitored user's heart rate by detecting light projected at the monitored user, such detected heart rate data and/or other data may be communicated directly to the parent via transmitter module 220, for example at the parent's smartphone and/or at a control panel located near the parent. In this way, the parent may monitor the baby's status in real-time.

In other embodiments, heart rate detection module 215 may receive data associated with the monitored baby from receiver module 210, and may perform one or more operations based at least in part on the data to derive an alert. For example, where receiver module 210 transmits physiological data, such as the baby's heart rate, to heart rate detection module 215, heart rate detection module 215 may compare the received heart rate data with a heart rate threshold to determine whether the baby is experiencing a heart rate event. This heart rate threshold may be based upon heart rate parameters inputted by system users, for example at a control panel or other component of the automation system, or may be based upon an accepted threshold, for example programmed into the automation system based on the size, age, and/or weight of the baby (among other factors) and standard heart rates and/or heart rate patterns for comparable babies and/or other people. Thus, where receiver module 210 communicates a detected heart rate below or above the heart rate threshold, heart rate detection module 215 may determine that the baby is experiencing a heart rate event, and may initiate and/or derive an alert accordingly. This alert may be communicated to transmitter module 220 for transmission to the parent, another monitoring user, and/or a device.

In some embodiments, the operations of heart rate detection module 215 may be performed in part or entirely by physiological parameter module 445, as discussed below in further detail with respect to FIG. 4.

The transmitter module 220 may transmit the one or more signals received from other components of the apparatus 205. As described above, the transmitter module 220 may transmit data received from receiver module 210 directly to the monitoring user without further processing by heart rate detection module 215 in some examples, or in other examples may transmit an alert derived by heart rate detection module 215 as a result of heart rate detection module 215 processing the data received from receiver module 210. In some examples, the transmitter module 220 may be collocated with the receiver module 210 in a transceiver module. Data or signals transmitted from transmitter module 220 may be received by a parent or other monitoring user at one or more components of the automation system, such as a control panel or a speaker unit, or may be received at a smartphone or a personal computing device associated with one or more home occupants and/or another monitoring user.

Figure 3:
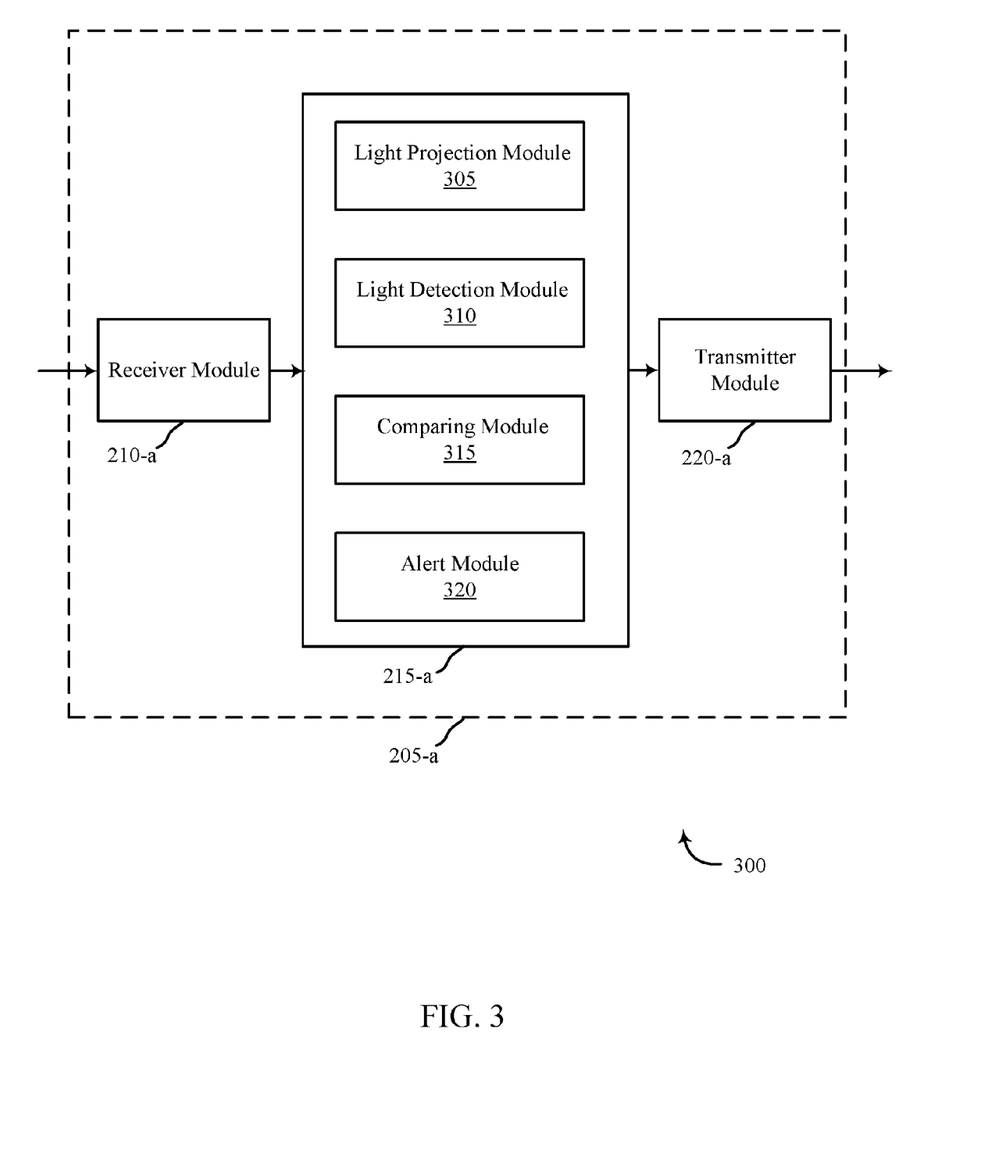
FIG. 3 shows a block diagram of a device relating to a home security and/or automation system, in accordance with various aspects of this disclosure.

FIG. 3 shows a block diagram 300 of an apparatus 205-*a* for use in automation and/or security systems, in accordance with various examples. The apparatus 205-*a* may be an example of one or more aspects of any of a control panel 130, one or more sensor units 110, local computing device 115, 120, and/or remote computing device 140 described with reference to FIG. 1, among others. It may also be an example of an apparatus 205 described with reference to FIG. 2. The apparatus 205-*a* may include a receiver module 210-*a*, a heart rate detection module 215-*a*, and/or a transmitter module 220-*a*, which may be examples of the corresponding modules of apparatus 205. The apparatus 205-*a* may also include a processor. Each of these components may be in communication with each other. The heart rate detection module 215-*a* may include one or more of a light projection module, a light detection module, a comparing module, and/or an alert module. The receiver module 210-*a* and the transmitter module 220-*a* may perform the functions of the receiver module 210 and the transmitter module 220 of FIG. 2, respectively.

The components of the apparatus 205-*a* may, individually or collectively, be implemented using one or more application-specific integrated circuits (ASICs) adapted to perform some or all of the applicable functions in hardware. Alternatively, the functions may be performed by one or more other processing units (or cores), on one or more integrated circuits. In other examples, other types of integrated circuits may be used (e.g., Structured/Platform ASICs, Field Programmable Gate Arrays (FPGAs), and other Semi-Custom ICs), which may be programmed in any manner known in the art. The functions of each module may also be implemented—in whole or in part—with instructions embodied in memory formatted to be executed by one or more general and/or application-specific processors.

Where apparatus 205-*a* is an example of a video component of a sensor unit 110 as discussed with respect to FIG. 1, light projection module 305 may be a component of the sensor unit (apparatus 205-*a*) and be configured to project light from the sensor unit toward the monitored baby or other home occupant/user. Light detection module 310 may then be configured to detect the light projected onto and/or reflected back from the monitored user, for example using a video lens and/or other components of the apparatus 205-*a*. This detection of the projected light may allow apparatus 205-*a* to "visualize" and/or determine a representation of the monitored baby's heart rate and/or other physiological parameter, based on detecting the visual pulse of blood under the baby's skin, as illuminated by the projected light.

In other embodiments, where apparatus 205-*a* is an example of any of a control panel 130 or local computing device 115, 120, as described with reference to FIG. 1, light projection module 305 may not be a component of the heart rate detection module 215-*a*, as the apparatus 205-*a* itself may not project the light. Instead, a sensor unit collocated with the monitored baby may project the light. Similarly, light detection module 310 may not be a component of the heart rate detection module 215-*a*, but instead the projected light may be detected by the sensor unit, and then transmitted to receiver module 210-*a* and on to heart rate detection module 215-*a* for processing. Other variations are also envisioned.

Comparing module 315 may be configured to compare the detected heart rate and/or other physiological characteristic of the monitored baby with a predetermined threshold (e.g., a heart rate threshold). Where apparatus 205-*a* is an example of a sensor unit, comparing module 315 may receive the detected heart rate data directly from light detection module 310. In other examples, where apparatus 205-*a* is an example of a control panel or local computing device, comparing module 315 may receive the detected heart rate data from a sensor unit collocated with the baby, via receiver module 210-*a*. In some examples, the heart rate threshold may be determined based on inputted user preferences, for example at a control panel and/or a smartphone device, while in other examples, the heart rate threshold may be determined based on commonly used standards for baby monitoring (e.g., from a database, from an Internet source, etc.) and/or from system-learned past monitoring preferences and/or settings. In some examples, where comparing module 315 determines that the heart rate data associated with the monitored baby constitutes an event, this event determination may be communicated to alert module 320 to derive an alert. In other examples, heart rate data associated with the monitored baby that is determined to constitute an event may be communicated directly to the monitoring parent via transmitter module 220-*a*, for example as a live video stream or an audio siren.

Alert module 320 may be configured to receive data from comparing module 315 indicating that an event has occurred and/or is occurring, and may derive an alert accordingly. The alert may take the form of an audio alert, such as a siren or prerecorded audio message, among others; a visual alert, such as a flashing light or message displayed on a control panel or personal computing device, among others; and/or a haptic alert, such as a vibration at the monitoring parent's smartphone, among others. The alert derived at alert module 320, in any form, may be communicated to the monitoring users, where the monitoring users may be one or more parents and/or caretakers, via transmitter module 220-*a*.

In some embodiments, the operations of heart rate detection module 215-*a* may be performed in part or entirely by physiological parameter module 445, as discussed below in further detail with respect to FIG. 4.

Figure 4:
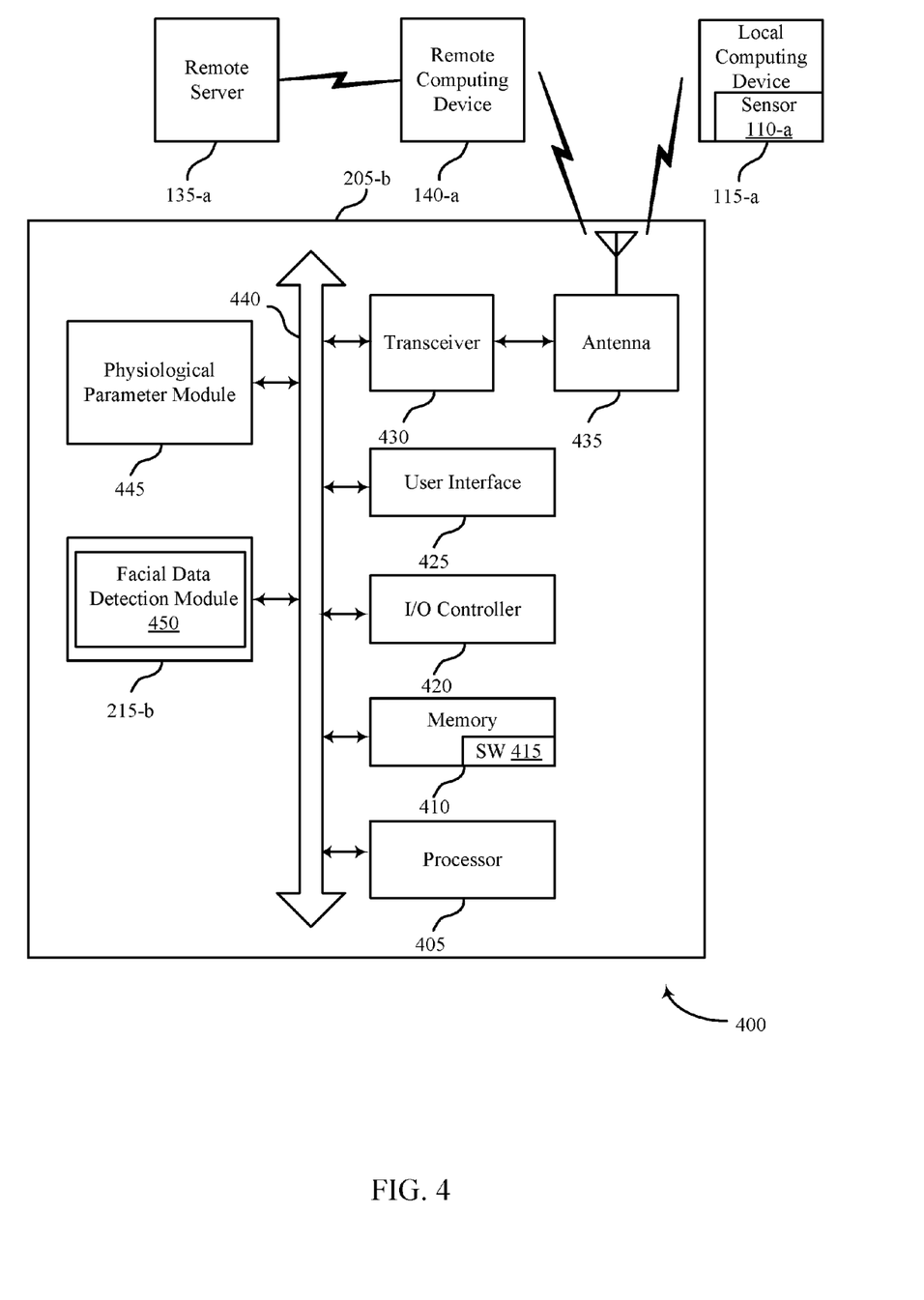
FIG. 4 shows a block diagram relating to a home security and/or automation system, in accordance with various aspects of this disclosure.

FIG. 4 shows a system 400 for use in security and/or automation systems, in accordance with various examples. System 400 may include an apparatus 205-*b*, which may be an example of one or more aspects of any of a control panel 130, one or more sensor units 110, local computing device 115, 120, and/or remote computing device 140 described with reference to FIG. 1, among others. Apparatus 205-*b* may also be an example of one or more aspects of apparatus 205 and/or 205-*a* of FIGS. 2 and 3.

Apparatus 205-*b* may include physiological parameter module 445. Physiological parameter module 445 may be configured to detect other physiological data associated with the monitored baby beyond the heart rate data detected by heart rate detection module 215, 215-*a* discussed with respect to FIGS. 2 and 3.

Physiological data may be detected directly by physiological parameter module 445, for example where apparatus 205-*b* is an example of a sensor unit, and/or physiological data may be received by physiological parameter module 445 from a separate one or more sensor units, for example where apparatus 205-*b* is a control panel or local computing device. The physiological data detected by physiological parameter module 445 may include any of respiration rate, body temperature, movement data, and/or auditory data associated with the monitored baby (among others), or a combination thereof. In some examples, this physiological data may be used to bolster or undermine an alert derived based on comparing the detected heart rate data with a predetermined heart rate threshold. For example, heart rate detection module 215, 215-*a*, as described with reference to FIGS. 2 and 3, may have detected that the monitored child's heart rate exceeds a predetermined heart rate threshold, and derived an alert condition based at least in part on the exceeded threshold. However, physiological parameter module 445 may simultaneously detect that the monitored child is playing, for example based on detected audio and/or other data indicating the child is laughing, moving around, engaging in recognized activities and/or positions, and/or the like. Based on this data, physiological parameter module 445 may determine that the cause of the child's increased heart rate is not cause for alert, and may accordingly bypass the derived alert.

Apparatus 205-*b* may also include facial data detection module 450, configured to detect facial data associated with the monitored baby or other user, identify the monitored baby, and associate that identity with the derived alert. For example, facial data detection module 450 may be configured to identify face shape, location of features, eye color, or the like, and to compare this data with a database of known face shape, location of features, eye color, and the like data associated with known individuals. Based on this comparing, facial data detection module 450 may derive an identity of the monitored user. This may be particularly useful in instances where multiple children are being monitored simultaneously in the same and/or different areas in a home or an office. For example, one or multiple sensor units may be positioned in a room with multiple children, and may monitor the heart rates or other physiological data associated with each child. By identifying each individual monitored child, should the one or more sensor units detect an alert condition with regard to one or more child's heart rate, that alert condition may be communicated to the parents with the identity of that child so that appropriate, targeted care may be administered. In some examples, the identity of the monitored baby may be compared with inputted preferences, settings, functions, operations, urgency of an alert, physiological data, or other data, or some combination thereof, and/or other information regarding alerts associated with the monitored user(s). For example, an alert threshold for increased heart rate may be lower for a baby in the room, while an alert threshold for increased heart rate may be comparatively higher for a toddler in the room, where the toddler is more likely to be more active and maintain a higher heart rate without risk.

Apparatus 205-b may also include components for bi-directional data communications including components for transmitting communications and components for receiving communications. For example, apparatus 205-b may communicate bi-directionally with one or more of local computing device 115-a, one or more sensor units 110-a, remote computing device 140-a, and/or remote server 135-a, which may be examples of the local computing device 115, one or more sensor units 110, and server 135 of FIG. 1, among others. This bi-directional communication may be direct (e.g., apparatus 205-b communicating directly with remote computing device 140-a) and/or indirect (e.g., apparatus 205-b communicating indirectly with remote server 135-a through remote computing device 140-a).

Apparatus 205-b may also include a processor module 405, and memory 410 (including software/firmware code (SW) 415), an input/output controller module 420, a user interface module 425, a transceiver module 430, and one or more antennas 435, each of which may communicate—directly or indirectly—with one another (e.g., via one or more buses 440). The transceiver module 430 may communicate bi-directionally—via the one or more antennas 435, wired links, and/or wireless links—with one or more networks or remote devices as described above. For example, the transceiver module 430 may communicate bi-directionally with one or more of local computing device 115-a, remote computing device 140-a, and/or remote server 135-a. The transceiver module 430 may include a modem to modulate the packets and provide the modulated packets to the one or more antennas 435 for transmission, and to demodulate packets received from the one or more antenna 435. While a an apparatus (e.g., 205-b) may include a single antenna 435, the apparatus may also have multiple antennas 435 capable of concurrently transmitting or receiving multiple wired and/or wireless transmissions. In some embodiments, one element of apparatus 205-b (e.g., one or more antennas 435, transceiver module 430, etc.) may provide a direct connection to a remote server 135-a via a direct network link to the Internet via a POP (point of presence). In some embodiments, one element of apparatus 205-b (e.g., one or more antennas 435, transceiver module 430, etc.) may provide a connection using wireless techniques, including digital cellular telephone connection, Cellular Digital Packet Data (CDPD) connection, digital satellite data connection, and/or another connection.

The signals associated with system 400 may include wireless communication signals such as radio frequency, electromagnetics, local area network (LAN), wide area network (WAN), virtual private network (VPN), wireless network (using 802.11, for example), 345 MHz, Z-WAVE®, cellular network (using 3G and/or LTE, for example), and/or other signals. The one or more antennas 435 and/or transceiver module 430 may include or be related to, but are not limited to, WWAN (GSM, CDMA, and WCDMA), WLAN (including BLUETOOTH® and Wi-Fi), WMAN (WiMAX), antennas for mobile communications, antennas for Wireless Personal Area Network (WPAN) applications (including RFID and UWB). In some embodiments, each antenna 435 may receive signals or information specific and/or exclusive to itself. In other embodiments, each antenna 435 may receive signals or information not specific or exclusive to itself.

In some embodiments, one or more sensor units 110-a (e.g., motion, audio, video, physiological, and/or one or more other sensors) may connect to some element of system 400 via a network using one or more wired and/or wireless connections.

In some embodiments, the user interface module 425 may include an audio device, such as an external speaker system, an external display device such as a display screen, and/or an input device (e.g., remote control device interfaced with the user interface module 425 directly and/or through input/output controller module 420).

One or more buses 440 may allow data communication between one or more elements of apparatus 205-b (e.g., processor module 405, memory 410, input/output controller module 420, user interface module 425, etc.).

The memory 410 may include random access memory (RAM), read only memory (ROM), flash RAM, and/or other types. The memory 410 may store computer-readable, computer-executable software/firmware code 415 including instructions that, when executed, cause the processor module 405 to perform various functions described in this disclosure (e.g., detect light projected toward and/or reflected from a monitored user, detect a heart rate and/or other physiological information of the monitored user based on the detected projected light, compare the detected heart rate with a predetermined heart rate threshold, initiate an alert, etc.). Alternatively, the computer-executable software/firmware code 415 may not be directly executable by the processor module 405 but may cause a computer (e.g., when compiled and executed) to perform functions described herein. Alternatively, the computer-readable, computer-executable software/firmware code 415 may not be directly executable by the processor module 405 but may be configured to cause a computer (e.g., when compiled and executed) to perform functions described herein. The processor module 405 may include an intelligent hardware device, e.g., a central processing unit (CPU), a microcontroller, an application-specific integrated circuit (ASIC), etc.

In some embodiments, the memory 410 may contain, among other things, the Basic Input-Output System (BIOS) which may control basic hardware and/or software operation such as the interaction with peripheral components or devices. For example, the physiological parameter module 445 to implement the present systems and methods may be stored within the memory 410. Applications resident with system 400 are generally stored on and accessed via a non-transitory computer readable medium, such as a hard disk drive or other storage medium. Additionally, applications may be in the form of electronic signals modulated in accordance with the application and data communication technology when accessed via a network interface (e.g., transceiver module 430, one or more antennas 435, etc.).

Many other devices and/or subsystems may be connected to, or may be included as, one or more elements of system 400 (e.g., entertainment system, computing device, remote cameras, wireless key fob, wall mounted user interface device, cell radio module, battery, alarm siren, door lock, lighting system, thermostat, home appliance monitor, utility equipment monitor, and so on). In some embodiments, all of the elements shown in FIG. 4 need not be present to practice the present systems and methods. The devices and subsystems may be interconnected in different ways from that shown in FIG. 4. In some embodiments, an aspect of some operation of a system, such as that shown in FIG. 4, may be understood in the art and is not discussed in detail in this application. Code to implement the present disclosure may be stored in a non-transitory computer-readable medium such as one or more of memory 410 or other memory. The operating system provided on input/output controller module 420 may be iOS®, ANDROID®, MS-DOS®, MS-WINDOWS®, OS/2®, UNIX®, LINUX®, or another known operating system.

The transceiver module 430 may include a modem configured to modulate the packets and provide the modulated packets to the antennas 435 for transmission and/or to demodulate packets received from the antennas 435. While the apparatus (e.g., 205-b) may include a single antenna 435, the apparatus (e.g., 205-b) may have multiple antennas 435 capable of concurrently transmitting and/or receiving multiple wireless transmissions.

The apparatus 205-b may include a heart rate detection module 215-b, which may perform the functions described above for the heart rate detection modules 215, 215-a of apparatus 205, 205-a of FIGS. 2 and 3, among others.

Figure 5:
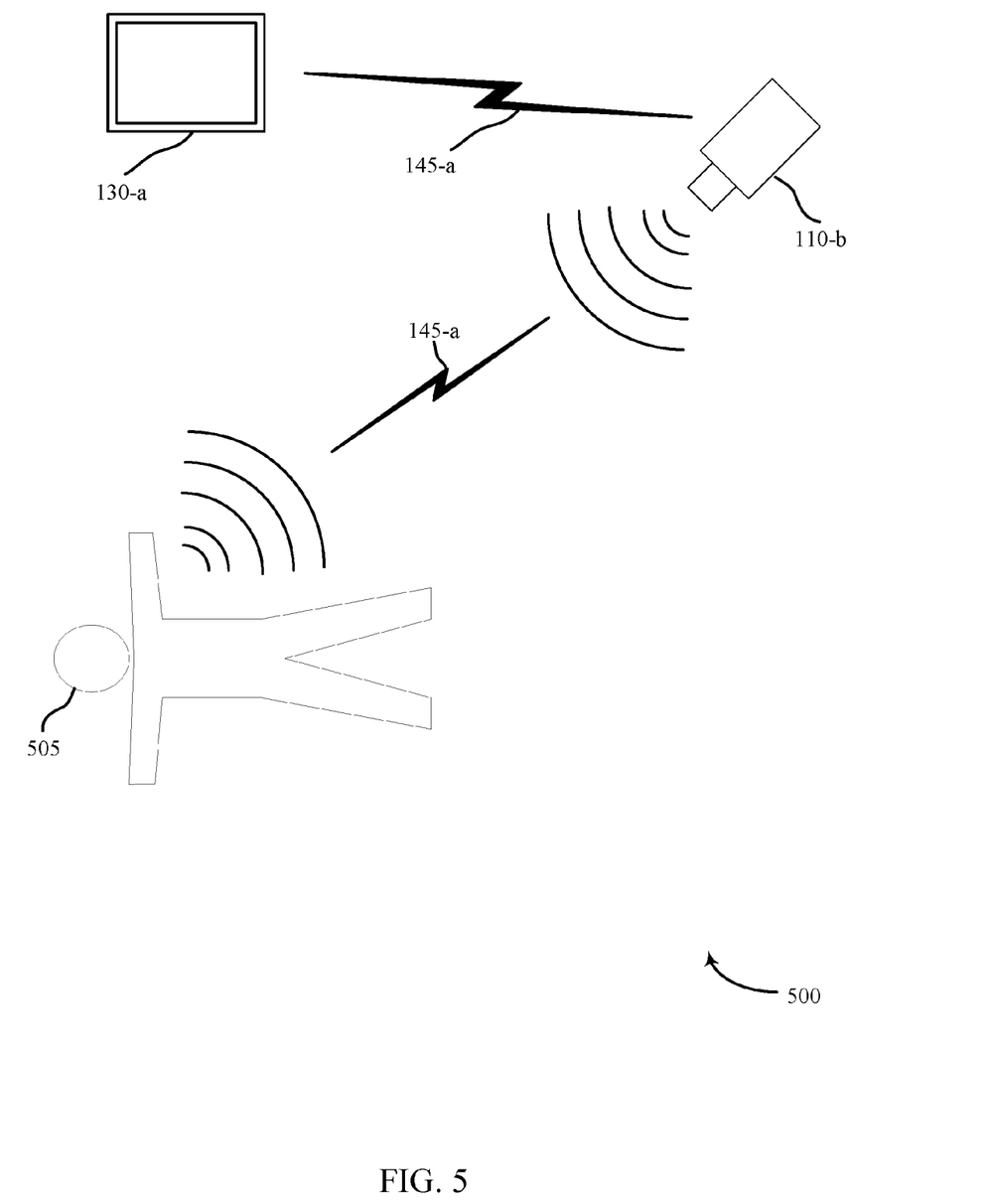
FIG. 5 shows a block diagram illustrating one embodiment of a home security and/or automation system, in accordance with various aspects of this disclosure.

FIG. 5 is a block diagram illustrating an example of the baby monitoring system 500. In the illustrated example, one or more sensor units 110-b may detect data associated with a baby and/or other monitored occupant 505. For example, sensor unit 110-b, which may be an example of one or more sensor units 110 described with respect to FIG. 1, may detect audio and/or video data, physiological data, movement data, environmental data, and/or the like. In the illustrated example, sensor unit 110-b may be and/or include a video camera or video monitoring component of the home automation system. Sensor unit 110-b may be configured to project a light toward the monitored baby 505. Sensor unit 110-b may be further configured to detect the projected light (whether from sensor unit 110-b and/or from one or more other components, such as an additional sensor unit 110-b), for example projected onto the monitored baby's 505 skin, and to detect a heart rate of the monitored baby 505 based at least in part on detecting the projected and/or reflected light.

In some examples, sensor unit 110-b may process the detected heart rate data associated with the monitored baby 505 in order to derive an event condition. In some examples, this processing may include comparing the data and/or a subset of the data to one or more conditions, such as a predetermined heart rate threshold based at least in part on the detected projected light.

In other examples, sensor unit 110-b may transmit the detected heart rate data and/or other information directly on to control panel 130-a, which may be an example of control panel 130 described with reference to FIG. 1. Although illustrated as a control panel 130-a in baby monitoring system 500, in other examples sensor unit 110-a may communicate detected heart rate data to a local computing device or remote computing device (e.g., 115, 120 and/or 140), as previously discussed. Upon receiving the detected heart rate data (among other data types), control panel 130-a may also either derive an event condition, and/or may communicate the detected heart rate data directly to a parent and/or other monitoring user. Where control panel 130-a derives an event condition, as discussed above with respect to FIGS. 2 and 3, control panel 130-a may receive heart rate data associated with the baby and may compare the received data with a predetermined event threshold to determine whether an event condition exists. Where control panel 130-a determines that an event condition exists, control panel 130-a may further determine whether to derive an alert, or to communicate the data associated with the event condition to the monitoring user, based on inputted user preferences. Thus, control panel 130-a may communicate to the monitoring user a live audio and/or video stream in some examples, or may communicate an alert, for example in the form of an audio or haptic alarm, to the monitoring user in other examples.

Control panel 130-a may further receive, determine, derive, calculate, compare, correlate, and/or evaluate specific identity information associated with the monitored baby 505. Control panel 130-a may utilize this identity information in order to communicate specific alerts associated with the identity of the monitored baby 505 to a parent and/or other monitoring user.

Figure 6:
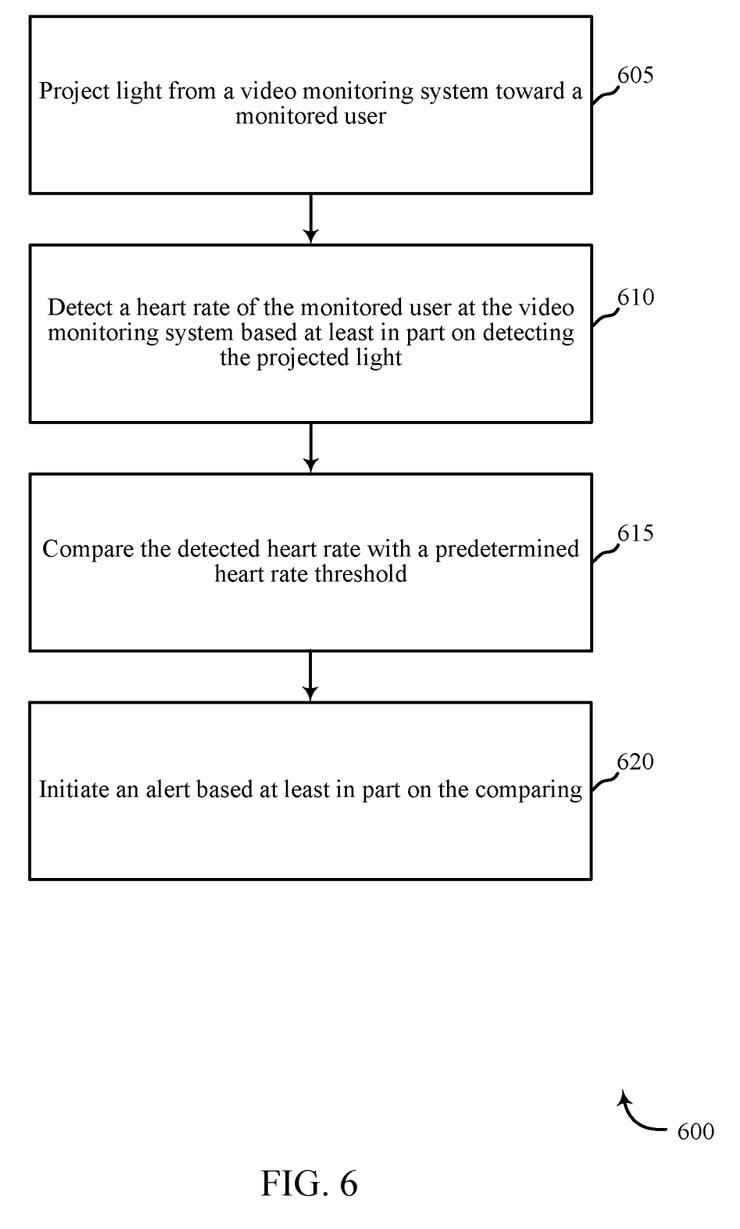
FIG. 6 is a flow chart illustrating an example of a method relating to a home security and/or automation system, in accordance with various aspects of this disclosure.

FIG. 6 is a flow chart illustrating an example of a method 600 for monitoring baby physical characteristics, in accordance with various aspects of the present disclosure. For clarity, the method 600 is described below with reference to aspects of one or more of the sensor units 110, local computing devices 115, 120, control panel 130, or remote computing device 140 described with reference to FIG. 1, and/or aspects of apparatus 205, 205-a described with reference to FIGS. 2 and 3, among others. In some examples, a control panel may execute one or more sets of codes to control the functional elements of the one or more sensor units to perform the functions described below. Additionally or alternatively, the control panel may perform one or more of the functions described below using special-purpose hardware.

At block 605, the method 600 may include projecting a light from a video monitoring system toward a monitored user. In some examples, the monitored user may be a baby, while in other examples, the monitored user may be an ill or elderly home occupant, or any other occupant in need of monitoring.

In some examples, a plurality of sensors associated with the video monitoring system may be positioned throughout the home, and may each monitor the user sequentially as he moves about the home. For example, a video monitor in the monitored user's bedroom may project light toward the monitored user while he sleeps in his room, while a separate video monitor may project light toward the monitored user while he plays in the living room. This projection of light may occur on a continuous basis in some examples, or may occur at predetermined intervals in other examples. Monitoring the user at predetermined intervals of time may be useful to limit energy waste, and may allow for thorough, but not overly redundant, monitoring. In this way, the user may be monitored on a continuous basis, regardless of his position in the home.

At block 610, the method 600 may include detecting a heart rate of the monitored user at the video monitoring system based at least in part on detecting the projected light. The video monitoring system may detect the light projected on the skin of the monitored user, and may detect the monitored user's heart rate by modeling and/or "visualizing" the blood pumping under the user's illuminated skin. In particular, the video monitoring system may capture a video detecting light projected on the monitored user's skin. The captured video may be analyzed to detect changes in coloration of individual pixels in the video, where the changes in coloration are associated with blood entering and leaving the area associated with the pixels. These changes in coloration may indicate movement of blood under the user's skin, and thus the changes in pixel coloration may be utilized to derive a pulse rate/heart rate of the monitored user.

At block 615, the method 600 may include comparing the detected heart rate with a predetermined heart rate threshold. As previously discussed, the predetermined heart rate threshold may be inputted by a user in some examples, may be programmed into the monitoring system in other examples, and/or may be drawn from a public source, such as an Internet webpage, in still other examples. In some examples, the method may include reacting to a ranked order involving multiple thresholds. For example, a user-inputted threshold may have a lower numerical threshold (or other threshold) than that derived from a public source. The related components may provide a first alert type and/or severity when a baby's heart rate and/or other physiological characteristic exceeds the first threshold and may provide a second alert type and/or severity when a baby's heart rate and/or other physiological characteristic exceeds the second threshold. In some cases, the first alert type and/or severity may be different from the second alert type and/or severity. This may include an audio alert and/or a video alert, among others.

At block 620, the method 600 may include initiating an alert based at least in part on the comparing. The alert may be communicated to an interested user in any form, such as a visual alert at a control panel, a haptic alert at a smartphone, an auditory alert at a personal computing device or from the sensor detecting the alert condition, and/or other examples. In this way, an interested user may be alerted to a potentially dangerous physiological state of the monitored user, without the need for body-worn sensors on the monitored user.

Figure 7:
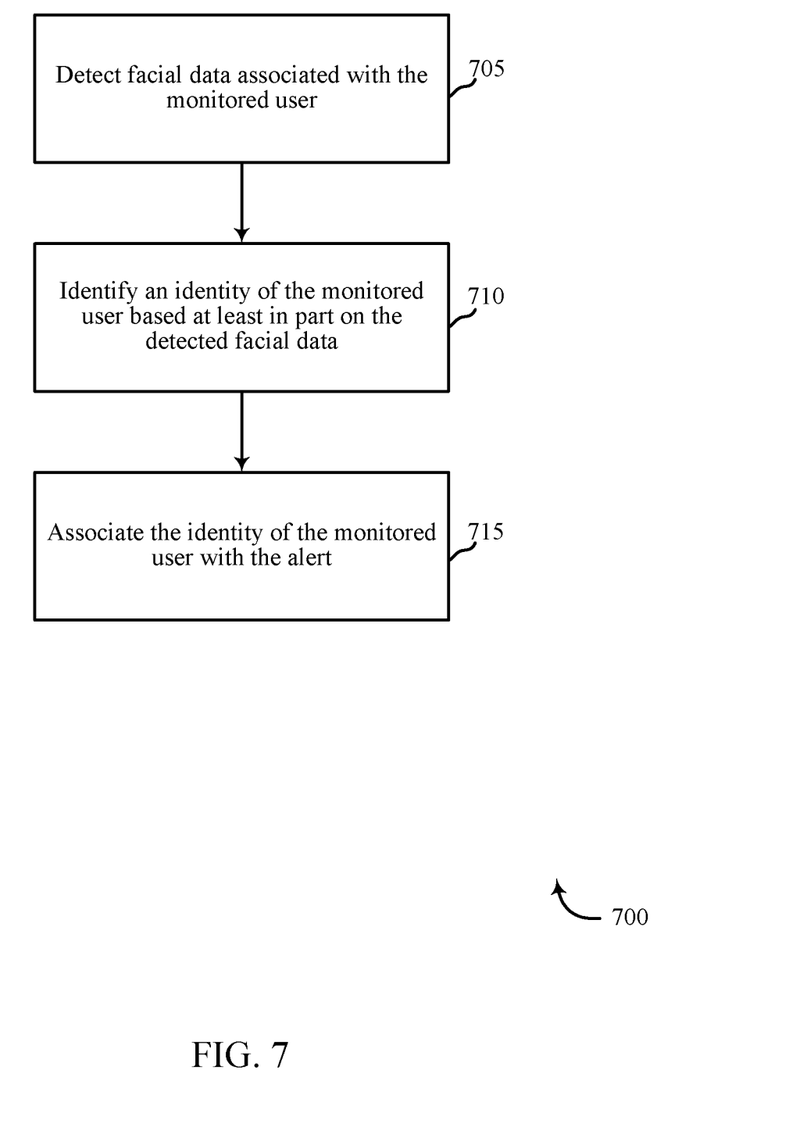
FIG. 7 is a flow chart illustrating an example of a method relating to a home security and/or automation system, in accordance with various aspects of this disclosure.

FIG. 7 is a flow chart illustrating an example of a method 700 for monitoring baby physical characteristics, in accordance with various aspects of the present disclosure. For clarity, the method 700 is described below with reference to aspects of one or more of the sensor units 110, local computing devices 115, 120, control panel 130, or remote computing device 140 described with reference to FIG. 1, and/or aspects of apparatus 205, 205-a described with reference to FIGS. 2 and 3, among others. In some examples, a control panel may execute one or more sets of codes to control the functional elements of the one or more sensor units to perform the functions described below. Additionally or alternatively, the control panel may perform one or more of the functions described below using special-purpose hardware.

At block 705, the method 700 may include detecting facial data associated with the monitored user. This detection of facial data may be achieved by any known facial recognition systems or methods. The detection may be performed by the video monitoring system from which light is projected toward the monitored user in some examples, or may be performed by a separate sensor unit collocated with the monitored user in other examples.

At block 710, the method 700 may include identifying an identity of the monitored user based at least in part on the detected facial data. Again, this identification of the monitored user may be achieved by facial recognition systems and methods. In other examples, the identity of the monitored user may be determined using other user identification methods, such as by identifying a smartphone or device associated with the monitored user, detecting an RFID signal from a device associated with the monitored user, utilizing voice recognition methods, or the like. The identification may be performed by the video monitoring system from which light is projected toward the monitored user in some examples, may be performed by a separate sensor unit collocated with the monitored user in other examples, and/or may be performed by a remotely located component of the home automation system, such as a control panel, and/or by a personal computing device, in other examples.

At block 715, the method 700 may include associating the identity of the monitored user with the alert. In this way, when an alert condition is derived based at least in part on comparing the detected heart rate of the monitored user with a predetermined heart rate threshold, the initiated alert may be communicated to a parent or other monitoring user along with the identity of the monitored user experiencing the alert condition. As previously discussed, this may be particularly important in instances where more than one user is being monitored in the same home.

In some examples, aspects from two or more of the methods 600 and 700 may be combined, omitted, and/or separated. It should be noted that the methods 600 and 700 are just example implementations, and that the operations of the methods 600 and 700 may be rearranged or otherwise modified such that other implementations are possible.

The detailed description set forth above in connection with the appended drawings describes examples and does not represent the only instances that may be implemented or that are within the scope of the claims. The terms "example" and "exemplary," when used in this description, mean "serving as an example, instance, or illustration," and not "preferred" or "advantageous over other examples." The detailed description includes specific details for the purpose of providing an understanding of the described techniques. These techniques, however, may be practiced without these specific details. In some instances, known structures and apparatuses are shown in block diagram form in order to avoid obscuring the concepts of the described examples.

Information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and components described in connection with this disclosure may be implemented or performed with a general-purpose processor, a digital signal processor (DSP), an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, and/or state machine. A processor may also be implemented as a combination of computing devices, e.g., a combination of a DSP and a microprocessor, multiple microprocessors, one or more microprocessors in conjunction with a DSP core, and/or any other such configuration.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope and spirit of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations.

As used herein, including in the claims, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination. Also, as used herein, including in the claims, "or" as used in a list of items (for example, a list of items prefaced by a phrase such as "at least one of" or "one or more of") indicates a disjunctive list such that, for example, a list of "at least one of A, B, or C" means A or B or C or AB or AC or BC or ABC (i.e., A and B and C).

In addition, any disclosure of components contained within other components or separate from other components should be considered exemplary because multiple other architectures may potentially be implemented to achieve the same functionality, including incorporating all, most, and/or some elements as part of one or more unitary structures and/or separate structures.

Computer-readable media includes both computer storage media and communication media including any medium that facilitates transfer of a computer program from one place to another. A storage medium may be any available medium that can be accessed by a general purpose or special purpose computer. By way of example, and not limitation, computer-readable media can comprise RAM, ROM, EEPROM, flash memory, CD-ROM, DVD, or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include compact disc (CD), laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The previous description of the disclosure is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not to be limited to the examples and designs described herein but is to be accorded the broadest scope consistent with the principles and novel features disclosed.

This disclosure may specifically apply to security system applications. This disclosure may specifically apply to automation system applications. In some embodiments, the concepts, the technical descriptions, the features, the methods, the ideas, and/or the descriptions may specifically apply to security and/or automation system applications. Distinct advantages of such systems for these specific applications are apparent from this disclosure.

The process parameters, actions, and steps described and/or illustrated in this disclosure are given by way of example only and can be varied as desired. For example, while the steps illustrated and/or described may be shown or discussed in a particular order, these steps do not necessarily need to be performed in the order illustrated or discussed. The various exemplary methods described and/or illustrated here may also omit one or more of the steps described or illustrated here or include additional steps in addition to those disclosed.

Furthermore, while various embodiments have been described and/or illustrated here in the context of fully functional computing systems, one or more of these exemplary embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may permit and/or instruct a computing system to perform one or more of the exemplary embodiments disclosed here.

This description, for purposes of explanation, has been described with reference to specific embodiments. The illustrative discussions above, however, are not intended to be exhaustive or limit the present systems and methods to the precise forms discussed. Many modifications and variations are possible in view of the above teachings. The embodiments were chosen and described in order to explain the principles of the present systems and methods and their practical applications, to enable others skilled in the art to utilize the present systems, apparatus, and methods and various embodiments with various modifications as may be suited to the particular use contemplated.

What is claimed is:

1. A method for security and/or automation systems, comprising:
    projecting light from a video monitoring system toward a monitored user;
    detecting a heart rate of the monitored user at the video monitoring system based at least in part on detecting the projected light;
    comparing the detected heart rate with a predetermined heart rate threshold;
    detecting a physiological parameter associated with the monitored user;
    comparing the detected physiological parameter with a predetermined physiological parameter threshold;
    bypassing an alert based at least in part on comparing the detected physiological parameter with the predetermined physiological parameter threshold;
    initiating the alert based at least in part on comparing the detected heart rate with the predetermined heart rate threshold;
    detecting facial data associated with the monitored user;
    identifying an identity of the monitored user based at least in part on the detected facial data; and
    associating the identity of the monitored user with the alert.

2. The method of claim 1, wherein the alert comprises:
    at least one of an auditory alert, or a visual alert, or a haptic alert, or a combination thereof.

3. The method of claim 1, wherein detecting the projected light comprises:

analyzing image data captured by the video monitoring system.

4. The method of claim 1, wherein projecting the light toward the monitored user comprises:
projecting the light continuously or projecting the light at predetermined intervals.

5. The method of claim 4, wherein detecting the heart rate of the monitored user comprises:
detecting the heart rate continuously or detecting the heart rate at predetermined intervals.

6. The method of claim 5, further comprising:
comparing the detected heart rate at a first time with the detected heart rate at a second time,
wherein the alert is initiated based at least in part on the comparing of the detected heart rate at the first time and the second time.

7. The method of claim 1, wherein detecting the physiological parameter comprises:
detecting at least one of a respiration rate, or a body temperature, or movement data, or auditory data, or a combination thereof.

8. The method of claim 1, further comprising:
initiating the alert based at least in part on comparing the detected physiological parameter with the predetermined physiological parameter threshold.

9. The method of claim 8, further comprising:
categorizing the alert based at least in part on comparing the detected physiological parameter with the predetermined physiological parameter threshold.

10. The method of claim 9, wherein the categorizing comprises:
defining the alert as any of a non-urgent alert, or an urgent alert, or an emergency alert, or a combination thereof.

11. The method of claim 1, further comprising:
determining a time period that the detected heart rate is outside the predetermined heart rate threshold;
comparing the time period to a time threshold; and
determining an alert severity based at least in part on the comparison of the time period to the time threshold.

12. The method of claim 1, wherein the physiological parameter associated with the monitored user is a first physiological parameter, the method further comprising:
detecting a second physiological parameter associated with the monitored user, the first physiological parameter being different from the second physiological parameter; and
correlating the first physiological parameter with the second physiological parameter,
wherein bypassing the alert is further based at least in part on the correlation of the first physiological parameter with the second physiological parameter.

13. An apparatus for security and/or automation systems, comprising:
a processor;
memory in electronic communication with the processor; and
instructions stored in the memory, the instructions being executable by the processor to:
project light from a video monitoring system toward a monitored user;
detect a heart rate of the monitored user at the video monitoring system based at least in part on detecting the projected light;
compare the detected heart rate with a predetermined heart rate threshold;
detect a physiological parameter associated with the monitored user;
compare the detected physiological parameter with a predetermined physiological parameter threshold;
bypass an alert based at least in part on comparing the detected physiological parameter with the predetermined physiological parameter threshold;
initiate the alert based at least in part on comparing the detected heart rate with the predetermined heart rate threshold;
detect facial data associated with the monitored user;
identify an identity of the monitored user based at least in part on the detected facial data; and
associate an identity of the monitored user with the alert.

14. The apparatus of claim 13, wherein the alert comprises:
at least one of an auditory alert, or a visual alert, or a haptic alert, or a combination thereof.

15. The apparatus of claim 13, wherein detecting the projected light comprises:
analyzing image data captured by the video monitoring system.

16. The apparatus of claim 13, wherein projecting the light toward the monitored user comprises:
projecting the light continuously or projecting the light at predetermined intervals.

17. The apparatus of claim 16, wherein detecting the heart rate of the monitored user comprises:
detecting the heart rate continuously or detecting the heart rate at predetermined intervals.

18. A non-transitory computer-readable medium storing computer-executable code, the code executable by a processor to:
project light from a video monitoring system toward a monitored user;
detect a heart rate of the monitored user at the video monitoring system based at least in part on detecting the projected light;
compare the detected heart rate with a predetermined heart rate threshold;
detect a physiological parameter associated with the monitored user;
compare the detected physiological parameter with a predetermined physiological parameter threshold;
bypass an alert based at least in part on comparing the detected physiological parameter with the predetermined physiological parameter threshold;
initiate the alert based at least in part on comparing the detected heart rate with the predetermined heart rate threshold;
detect facial data associated with the monitored user;
identify an identity of the monitored user based at least in part on the detected facial data; and
associate an identity of the monitored user with the alert.

* * * * *